(12) United States Patent
Altura (10) Patent No.: US 6,613,953 B1
(45) Date of Patent: Sep. 2, 2003

(54) INSULATOR-CONDUCTOR DEVICE FOR MAINTAINING A WOUND NEAR NORMAL BODY TEMPERATURE

(76) Inventor: Dan Altura, 731 N. La Brea Ave., No. 5, Los Angeles, CA (US) 90038

( * ) Notice: Subject to any disclaimer, the term of this patent is extended or adjusted under 35 U.S.C. 154(b) by 0 days.

(21) Appl. No.: 10/103,216

(22) Filed: Mar. 22, 2002

(51) Int. Cl.7 .................................................. A61F 13/00
(52) U.S. Cl. .............................. 602/43; 602/41; 602/58; 604/304
(58) Field of Search ................................ 602/41–43, 46, 602/48, 53, 56, 58, 60, 61; 128/82.1, 893; 607/1, 96, 108, 112, 114, 115; 604/304

(56) References Cited

U.S. PATENT DOCUMENTS

| | | | |
|---|---|---|---|
| 3,972,328 A | * | 8/1976 | Chen |
| 4,753,241 A | * | 6/1988 | Brannigan et al. |
| 5,531,670 A | * | 7/1996 | Westby |
| 5,534,021 A | * | 7/1996 | Dvoretzky et al. |
| 6,071,254 A | * | 6/2000 | Augustine |
| 6,113,561 A | * | 9/2000 | Augustine |
| 6,235,047 B1 | * | 5/2001 | Augustine et al. |

* cited by examiner

Primary Examiner—Nicholas D. Lucchesi
Assistant Examiner—Lalita M Hamilton
(74) Attorney, Agent, or Firm—Thomas I. Rozsa; Tony D. Chen (57) ABSTRACT

A wound treatment device which fits over standard bandages and covers both the wound area itself and major portions of the surrounding area of healthy skin of an extremity such as a leg, arm, or foot. The wound treatment device maintains the wound near normal body temperature (37° C.) by conserving and redistributing the body's own heat energy using a high efficiency thermal insulator to minimize heat loss from the wound and surrounding skin area and a high efficiency thermal conductor for distributing heat from the surrounding skin to the wound area. The wound treatment device avoids potential problems associated with external heat sources and provides for an ideal physiological environment for wound healing. The wound treatment device can be worn by the patient for extended periods of time during their regular daily routine without constant medical supervision. The wound treatment device can also store extra thermal energy generated by physical activity such as walking, cleaning, or bicycling.

31 Claims, 6 Drawing Sheets

INSULATOR-CONDUCTOR DEVICE FOR MAINTAINING A WOUND NEAR NORMAL BODY TEMPERATURE

FIELD OF THE INVENTION

This invention relates to wound treatment using an outer wound covering which both thermally insulates the wound and surrounding skin area to minimize heat loss and conducts heat from surrounding skin to the wound in order to maintain the wound close to normal body temperature.

BACKGROUND OF THE INVENTION

There are two types of common chronic wounds. One type termed a bed sore or pressure sore is caused by constant pressure applied to a part of a body when a patient has limited mobility in a hospital bed, wheel chair, etc. The pressure point reduces circulation to that part of the body resulting in lowering of temperatures (hypothermia), reduced physiological activity, and finally the breakdown of tissue at the pressure point causing a wound. A second type of chronic wound is caused by reduced vascular activity at the wound site which reduces the flow of oxygenated blood to the wound area (arterial) and or accumulation of body fluid at the wound site (venus). This second type of chronic wound has an underlying cause such as diabetes or artherosclerosis. Due to the lack of adequate blood circulation to the wound area, this area is typically at a lower temperature relative to healthy skin surrounding the wound. Healthy skin exhibits surface temperatures which are several degrees lower than the body core temperature of 37° C. due to heat loss to the environment. The temperature of the surface of a wound can be significantly lower than that of normal skin, sometimes approaching temperatures as low as the surrounding room air. The application of heat to a wound has been shown to increase blood flow to the wound thereby increasing oxygen concentration at the wound site, giving increased rates of fluid and waste removal from the wound and increased immune function.

The therapeutic application of heat to a wound has been common practice since ancient times. Various types of artificial heating have been used on wounds including such devices as hot water bottles, warming pads, and heating lamps. These kinds of therapies can result in the accidental burning of the wound or surrounding skin area or the excessive drying out of the wound. There has also been concern amongst medical practitioners that heating a wound above the core body temperature can result in accelerated growth of bacteria due to both the elevated temperature and the reduced capacity of a chronic wound to fight infection.

Heat loss from a wound is the result of heat transfer from the wound to the surrounding environment. Heat transfer can occur in three basic ways. The first type, conductive heat transfer, occurs when energy is transported from one body to another due to molecular vibration and interaction. An example of this kind of heat transfer is the hand touching a cold piece of metal where the molecules of the skin of the hand lose energy by inducing vibration in the atoms of the metal. The second kind of heat transfer is convection which is heat energy transport due to bulk fluid motion along the surface of a solid. An example is the "wind chill factor" where the motion of the air hitting the body removes additional heat and makes the outdoor temperature feel colder than it really is. Finally there is radiation heat transfer which results from the emission of electromagnetic waves from a surface. Heat eminating from a light bulb is an example of this kind of heat transfer. The third type of heat transfer is usually only significant at temperatures above 200 C. and is a minor component of overall heat transfer at room temperature up to normal body temperature. The body, which maintains a constant core temperature, utilizes blood flow as a heat transfer medium similar to water in a car's radiator. As it flows, the blood heats the body's extremities such as the leg, foot, or arm. At the same time the skin of these extremities is constantly losing heat to the environment primarily due to conduction and convection heat transfer. Chronic wounds, having impaired blood flow, tend to lose heat to the environment without getting enough heat replenishment from the blood.

Minimizing heat loss from a wound is an alternative method to maintain an elevated wound temperature without resorting to external heating devices. Westby et al (U.S. Pat. No. 5,531,670, 1996) describes a heat conserving bandage consisting of one or more heat reflecting layers which reflect radiation heat eminating from the body back in the direction of the body. The bandage wraps around muscle and bone tissue and is used for heat therapy on muscles or other internal organs on both animals and humans. It is not intended for use on skin wounds, which due to their location on the exterior of the body tend to lose significantly more heat than internal organs such as muscle. All the examples of therapy using the Westby patent related to internal organs such as muscle, ligaments etc. According to the patentees, the primary mechanism for heat preservation is the reflection of radiation heat back to the source. As stated above, radiation heat transfer is small compared to the other two heat transfer mechanisms for temperatures below 200° C. The patentees also mention the use of closed cell rubber as a thermal conduction insulator. There are much better barriers to conduction heat transfer available than the rubber material. Using the Westly bandage for skin wounds may result in substantial heat loss due to the location of the skin at the exterior of the body.

Adequate heat transfer at the site of a wound is the subject of several patents. Eidus (U.S. Pat. No. 3,596,657, August 1971) describes a thermally conductive surgical dressing consisting of conventional cotton gauze interwoven with high conductive metallic thread. The metallic thread offers high thermal conductivity for removing heat from a surgical wound or injecting heat into a surgical wound using either ice packs or heating packs. Augustine et al (U.S. Pat. No. 6,235,047, May 2001) describes a thermally conductive bandage consisting of a polymeric layer which absorbs water enhancing thermal conductivity. Both devices basically sit on the wound and immediate skin area (periwound) only. They do not extend to other skin areas in the general area of the wound. Since the Eidus device utilizes a mesh of cotton interwoven with metal thread, the thermal conductivity will still be significantly lower than for mesh made entirely of metal or a metal sheet. The Augustine device uses water as the primary thermal conductor. Water is a good thermal conductor compared to air but a very poor thermal conductor compared to all high thermal conductive metals such as silver, copper, gold, and aluminum. Aluminum which is the least efficient conductor of the metals mentioned above, still has a thermal conductivity which is almost 400 times greater than pure water (237 W/M oK for water). Neither of these two patents is intended to conserve body heat and distribute it to the wound. Both use external heat sources to heat the wound.

SUMMARY OF INVENTION

Medical research has found that the best conditions for wound healing are those which duplicate as closely as possible normal physiological conditions. This includes wound temperature, which is optimized when it is as near to the normal core physiological temperature of the human body (37° C.) as possible.

Due to the inadequate transfer of oxygenated blood to the area of chronic wounds, the temperature of the wound is normally below that of healthy skin in nearby locations. Even healthy skin exhibits surface temperatures which are below the body core temperature due to heat loss. This problem is exacerbated for chronic wounds at locations where the soft tissue is normally very thin, as in the shin of the leg, big toe or heel of the foot, and other areas where bond protrusions are very close to the outer skin. In order to bring the wound temperature as close to the body core temperature (37° C.) without the use of externally applied artificial heat, the present invention utilizes basic principles of heat transfer to both conserve body heat in the vicinity of the wound and to distribute it to the wound itself As mentioned earlier, the primary mechanism for heat loss in a wound and surrounding skin areas is conduction heat transfer. Radiation heat transfer only becomes significant at more elevated temperatures (200° C.). Unlike inventions cited above, which deal primarily with the reflection of radiant energy back to the wound, the present invention deals with conduction heat transfer, utilizes high efficiency insulators to prevent body heat from escaping and high efficiency conductors for distributing stored heat energy to the wound area. The bandage in the present invention covers not only the wound area but major portions of skin and muscle mass surrounding the wound in order to maximize the amount of heat which is conserved and then redirect the heat to the wound area.

Properties of thermal insulators which minimize conductive heat loss are well known. The best insulators are those with the lowest thermal conductivity. A vacuum is the best thermal insulator. Next to a vacuum, gases are a close second and are much better thermal insulators than liquids or solids. Of readily available gases, several exhibit very low thermal conductivities while at the same time being safe to use around humans. These include air, nitrogen, argon, carbon dioxide, krypton, and possibly the Freon family (CC13F). These gases can be obtained in various types of configurations where the solid content and conductivity of the gas housing is minimized in order to minimize heat conduction due to the solid. Furthermore, geometric configurations of the insulators can be modified in order to minimize heat loss from the wound and the surrounding skin areas based on heat transfer theory. Thermal conductivity values for these low conductivity gases are given below.

| Gas | Thermal conductivity (watt/M ° K at 27° C.) |
|---|---|
| air | 0.026 |
| nitrogen | 0.026 |
| argon | 0.018 |
| carbon dioxide | 0.017 |
| krypton | 0.010 (at 38° C.) |
| R11(CCl3F) | 0.007 |

Recent advances in materials science have resulted in a totally new class of materials called aerogels which have the lowest thermal conductivities of any solids available today. Aerogels are highly porous materials with pore sizes down in the nanometer range. Thermal conduction through the solid part of the aerogel is minimized by the small connections between particles making up the conduction path. Conduction by gas trapped in the pores of the aerogel is minimized because the extremely small pore size which is about the same length as the mean free path of the gas. Aerogels can be made from a variety of precurser materials including silica, alumina, titania, hafnium carbide, and carbon. Silica aerogel exhibit a typical thermal conductivity of about 0.017 W/M oK at 27° C. and 1 atmosphere pressure. When the pressure is reduced to about 0.1 atmosphere the conductivity drops dramatically to 0.009 W/M oK. Silica aerogels have recently become available which are very flexible and can be twisted and wrapped around solid objects similar to cloth. Aerogel thermal conductivity can be further decreased by substituting a low conductivity gas such as carbon dioxide instead of air, in the pores of the aerogel. The present invention describes the use of the flexible aerogel to minimize heat loss near the wound.

Since healthy skin located near a chronic wound, especially skin in areas where significant amounts of muscle are present such as the calf, exhibits significantly higher temperatures than the wound itself (due to the impaired blood transport to the wound area), the transfer of heat from the healthy skin areas to the wound would help ameliorate the hypothermia of the wound area and bring it closer to normal core body temperature thereby promoting natural physiological healing. This can be accomplished by using a flexible conductive sheath which totally surrounds the wound area, adjacent healthy skin, and adjacent muscle mass. Conductivity in the sheath can be optimized by using metals which exhibit the highest values of thermal conductivity including silver, gold, copper, aluminum or alloys of these metals. The conductance of heat to the wound area can further be optimized by using a conductor geometry and thickness which maximizes conduction heat transfer while at the same time being plyable enough to be applied directly to the skin. This high efficiency thermal conductor sits directly on portion of healthy skin near the wound and directly on top of a wound bandage or dressing in the wound area. Conduction from the wound through the wound bandage to the metal sheath can be optimized by reducing wound bandage thickness and/or using bandage materials such as hydrogels which load up with water or adding colloidial silver to the bandage material to increase overall bandage conductivity. Typical conductances for the high efficiency conductors mentioned above are as follows:

| Metal | Thermal conductivity (Watt/m ° K at 25° C.) |
|---|---|
| Silver | 429 |
| Gold | 318 |
| Copper | 401 |
| Aluminum | 237 |

A fairly new class of materials called carbon-carbon composites exhibit thermal conductivities 3 times as high as copper (1200 W/M oK). Using the carbon-carbon composites in formulating the conductive sheath can offer optimal heat transfer from the surrounding skin to the wound.

The combination of ultra high insulators to minimize heat loss from the wound area with high thermal conductors to maximize heat transfer to the wound area from surrounding healthy skin has been shown to increase wound temperature by as much as 3.7° C. and bring the wound temperature close to the normal physiological core temperature. The following temperature data were obtained for the shin area of a healthy leg when using a prototype of the insulator-conductor wound covering of the present invention. The wound covering was placed over a gauze pad covering the skin (wound area) and totally wrapped around the calf muscle.

Ambient temperature: 74.7° F. (23.7° C.)

Temperature at surface of gauze pad: 92.0° F. (33.3° C.)

Average temperature of gauze pad covered with insulator-conductor wound covering over 6 hour period: 96.5° F. (35.8° C.)

Tests conducted with a prototype insulator-conductor boot which fits over the foot and extends up to the calf of the foot, has shown an average temperature at the big toe (after an equilibration period of 40 minutes) of 97.3° F. (36.3° C.) as compared to an average temperature of the big toe with gauze pad of 90.7° F. (32.6° C.).

The present invention gives various geometries for the insulator-conductor wound covering for use on various parts of the body, including leg, knee, foot, arm, elbow, hand, hip area, and buttocks area. Various configurations of the insulator are presented including thickness, type of insulator gas, type of gas containment device, and use of aerogel insulator materials. Various configurations of the conductor include thickness, type of metal used, and geometric configuration used. The configuration of the insulator pad as compared to the conductor pad is also presented as is the use with various kinds of common wound bandages.

Some advantages of the insulator-conductor wound treatment device over current wound heating methodologies are as follows:

1. Maintains wound temperature close to normal body temperature without the use of external heaters thereby promoting wound healing under the most ideal physiological conditions.
2. Wound covering fits directly over various types of wound bandages and is easy to apply and wear, giving the patient full freedom of mobility and allowing for normal daily routine.
3. Wound covering can be worn for many hours a day giving maximum therapeutic effect.
4. Wound covering can be attached to all common chronic wounds in various parts of the body including leg, knee, foot, arm, elbow, hand, buttocks, and hip area.
5. Wound covering totally eliminates the possibility of electrical shock from electrical appliance attached to the patient.
6. Wound covering eliminates the possibility of overheating resulting in burning of skin tissue.
7. Wound covering eliminates the need for frequent visits to the clinic for application of heat therapy.
8. Wound covering is an easy to use as an elastic bandage thereby promoting acceptance by medical practitioners.
9. Wound covering stores and distributes heat generated from increased metabolism and blood flow due to activities such as walking, cleaning and bicycling thereby providing extra heat to the wound over an extended period of time.
10. Wound covering promotes natural healing close to the ideal physiological temperature.

Further features of the invention will become apparent from the attached drawings and description of an illustrative embodiment of the invention.

DETAILED DESCRIPTION OF A PREFERRED EMBODIMENT OF THE INVENTION

This invention is a wound covering which fits over standard or special purpose bandages, and covers both the wound area itself and major portions of the surrounding area of healthy skin of an extremity, such as a leg, arm, or foot, and maintains the wound close to normal body temperature by conserving and redistributing the body;s own heat energy by using a high efficiency thermal insulator to minimize heat loss from the wound and surrounding skin area, and a high efficiency thermal conductor for distributing heat from the surrounding skin to the wound area.

The wound covering consists of three basic elements; An outer layer of high efficiency thermal insulator constructed out of plyable low density foam which may be filled with a low thermal conductivity gas such as air, argon, carbon dioxide, krypton, nitrogen, or CC14F (Freon) or a gas under partial vacuum, an inner sheath of a high efficiency thermal conduction which consists of a thin sheath of high thermal conductor metal such as silver, gold, copper, aluminum, their alloys, or carbon-carbon composite that sits directly in contact with the wound bandage and a major portion of the surrounding healthy skin, and finally a strap used to securely wrap the wound covering around an appendage such as a leg, knee, foot, arm, elbow or hand at the location of the wound. All the elements are bonded to each other by using chemical adhesives or by mechanical bonding.

As alternatives to the use of straps for securing the wound covering to the person's body, the wound covering can be incorporated into an item of clothing worn by the person, e.g. a boot, glove, underpants, knee covering, or elbow covering.

Figure 1:
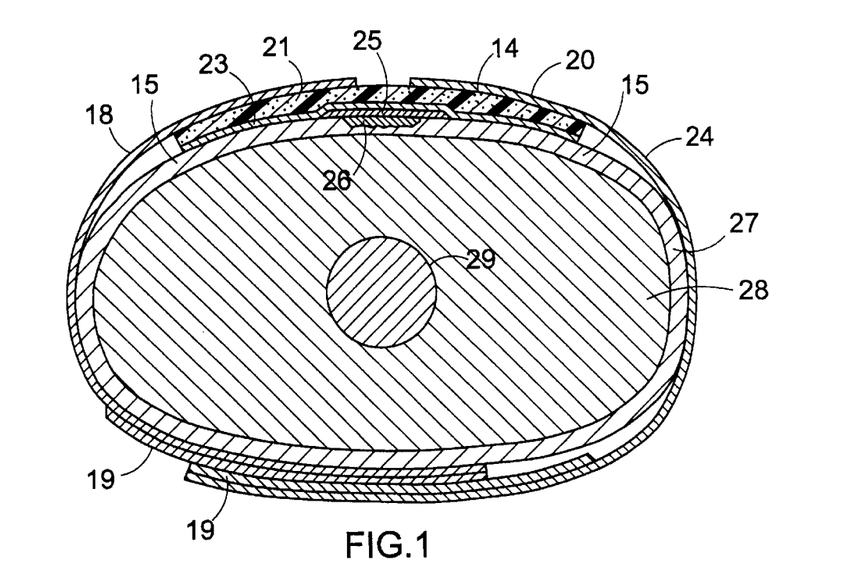
FIG. 1 is a sectional view taken on line 1—1 in FIG. 2, showing a wound treatment device of the present invention in place on an arm (or leg) of a person.
Figure 2:
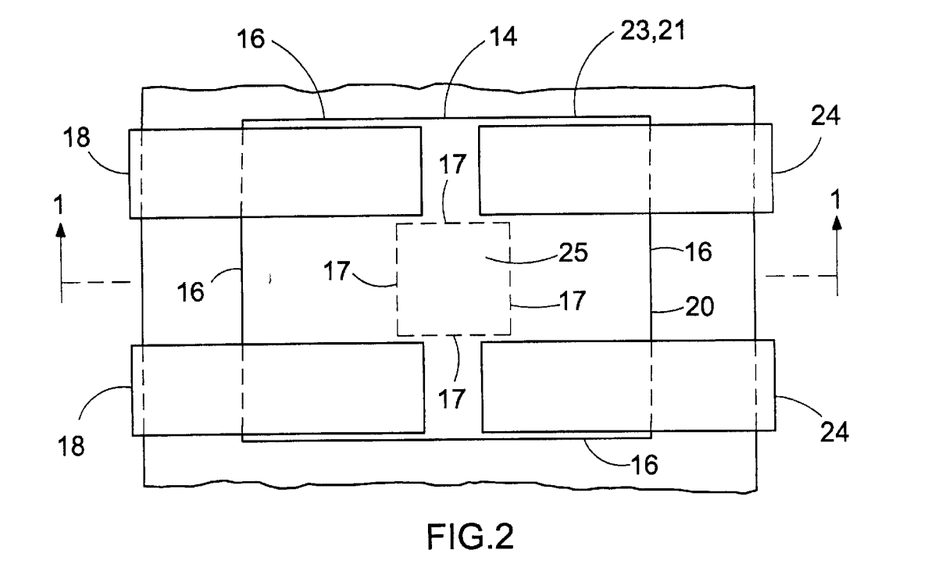
FIG. 2 is a plan view of the wound treatment device depicted in FIG. 1.

Referring to FIGS.1 and 2, there is shown a wound treatment device 20 for a skin wound 26 on a person's leg or arm. The human limb comprises a bone 29, within muscle 28 that is covered by a layer of skin (dermis and epidermis) 27. The wound 26 is covered by a bandage (or dressing) 25 that is slightly larger than the wound areawise, whereby the wound is completely covered by the bandage.

Bandage 25 can be a standard, or special purpose, bandage that includes e.g. multiple layers of gauze, a hydrated gauze type bandage, a hydrogel type bandage, a hydrocolloids type bandage, or a hydrated alginates type bandage.

A principal purpose of the invention is to treat the skin wound 26 so that the wound temperature is close to that of the normal core temperature 37° C. To aid in skin stabilizing the temperature of the skin wound, bandage 25 can be a thermally conductive bandage, e.g. a bandage containing colloidal silver suspended in a hydrogel within the pores of the bandage. At least some of the strands in the woven bandage can be formed of a thermally conductive material, such as-fine copper or silver wire.

Typically, the bandage will include a layer of adhesive tape for securing the bandage to the person's skin. However, the bandage can alternately be carried by an overlying covering 14 which is used in practice of the invention.

The invention is particularly concerned with a flexible insulative conductive covering 14 for bandage 25, whereby human body heat is prevented from escaping due to the insulative outer layer 21 and this heat being transported from the healthy skin around the wound to the wound by the conductive inner layer 23 from healthy skin surrounding wound 26 to bandage 25, thereby preventing heat loss out of the wound through the bandage. As shown in FIG. 1, covering 14 includes a thermally conductive inner layer 23 overlying bandage 25 and healthy areas of the person's skin surrounding wound 26. Covering 14 further includes a heat-insulating outer layer 21 adhered to the thermally-conductive inner layer.

Covering 14 is constructed so that heat from healthy skin areas 15 flows into the thermally conductive inner layer 23 of the covering so as to eventually reach the central portion of layer 23 that overlies bandage 25. The bandage is thereby heated so as to maintain wound 26 at close to that of normal core temperature 37° C.

Heat insulating outer layer 21 minimizes heat loss from the surrounding healthy skin and raises healthy skin areas 15 temperature to near that of normal core body temperature (37° C.) and maintains the thermally conductive inner layer 23 at approximately the same temperature as healthy skin areas 15, so that the temperature of inner layer 23 is stabilized or maintained relatively constant across the inner layer surface, from one edge of layer 15 across the layer 15 surface to the opposite edge.

The area of heat-insulating layer 21 is at least as great or greater as than the area of inner layer 23, so that the insulating layer completely covers the thermally-conductive layer.

In order for conductive layer 23 to perform its intended function the surface area of layer 23 is required to be several times the corresponding area of bandage 25. As shown in FIG. 2 of the drawings, peripheral edges 16 of layer 23 are spaced away from the peripheral edges 17 of bandage 25, so that the total surface area of conductive layer 23 is several times the corresponding surface area of the bandage. As depicted in FIG.2, the surface area of conductive layer. 23 is approximately twelve times the surface area of bandage 25.

The surface area of the conductive layer can be increased as to almost completely surround the human limb in FIG. 1. The surface area of conductive layer 23 should be several times the surface area of bandage 25, e.g. at least ten times. As previously noted, the area of insulative layer 21 is at least as great as or greater than that of layer 23, so that the insulating layer completely covers the conducting layer.

Heat conducting layer 23 can be formed of various thermally conductive materials, e.g. silver, gold, copper, aluminum, various metal alloys, or carbon composites in sheet form or fine mesh gauze form. The conductive material may be laminated onto a thin plastic backing sheet. One commercially available material is marketed under the tradename Mylar (aluminized). The conductive material can have a thickness of about 0.001 to 0.004 inches.

Preferably the thermally conductive material is in direct contact with the person's skin and bandage 25. However, a thin layer of cotton or nylon gauze can be provided on the conductive surface, if necessary to achieve a more comfortable feel on the person's s kin. To make covering 14 as flexible as possible, the conductive material on inner layer 23 can be subjected to various heat treating (annealing) operations.

Heat insulating layer 21 can be formed of various materials and porosities, in keeping with the necessary pliability and heat-containment (heat barrier) function. As shown in FIG. 1, layer 21 is an elastomeric foam having a closed cell character. Various foam materials can be used, e.g. polyurethane, polyvinyl chloride, polyethylene, natural rubber, or synthetic rubber. Preferably the foam cells are as large as possible, to minimize weight and to achieve a reasonably good insulating action. The foam cells can be filled with any of the high insulative gases, such as air, argon, carbon dioxide, krypton, nitrogen or freon to achieve maximum insulative properties. A smooth non-pervious skin (not shown) can be provided on the exposed surface of heat insulating layer 21, to seal the surface, enhance cleanability, and provide a better overall appearance.

The wound treatment device 20 can be retained on the person's body in various ways, e.g. adhesives, belts, etc. As shown in FIGS.1 and 2, the retaining mechanism includes a flexible strap assembly that comprises two parallel straps 24 extending rightwardly from covering 14, and two additional straps 18 extending leftwardly from covering 14, so that the free ends of straps 24 and 18 overlap. Terminal overlapping ends of the straps carry hook-and-loop fabric fastener patches 19, whereby the straps can be securely fastened together to secure the wound treatment device on the person's skin.

Hook-and-loop fabric fastener patches are commercially available under the tradename Velcro. The mating patches can be interlocked to achieve a pressure fit of wound, treatment device 20 on the person's skin.

Figure 3:
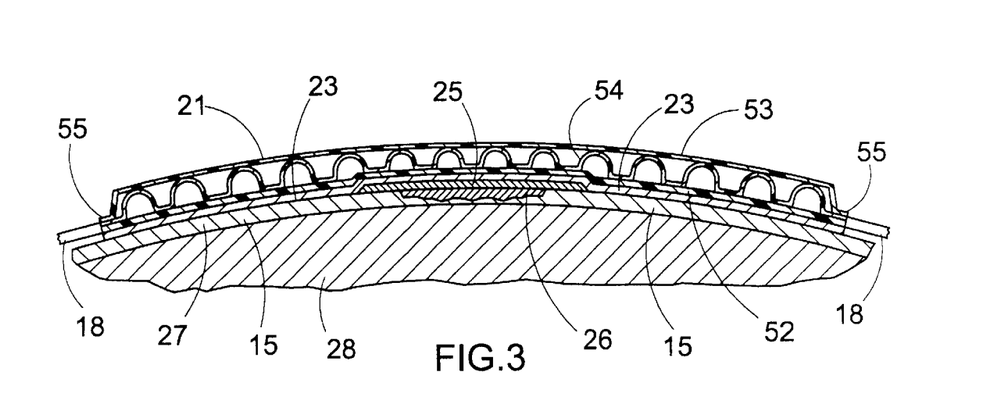
FIG. 3 is a fragmentary sectional view, taken in the same direction as FIG. 1, but showing another wound treatment device embodying the invention.

FIG. 3 fragmentarily shows a second embodiment of the invention wherein the heat-insulating layer 21 is formed of a laminated plastic sheet having plural closed bubbles spaced along the sheet surface. The laminated plastic sheet can be a commercially available packaging (cushioning) material sometimes called "bubble pack" or "bubble wrap".

As shown in FIG. 3, heat-insulating layer 21 includes a lower flexible plastic sheet 52 that is essentially flat, a second upper plastic sheet 53 that parallels sheet 52, and an intermediate plastic sheet 54 that is embossed to form regularly spaced bubbles across the sheet span. Edge areas 55 of sheet 53 are heat sealed to edge areas of sheet 52 to seal the bubble spaces from the ambient atmosphere. The bubbles can be filled with any of the high insulative gases such as air, argon, carbon dioxide, krypton, nitrogen or freon to achieve maximum insulative properties.

The bubble sheet insulator 21 of FIG. 3 is laminated to thermally-conductive sheet 23, to form a flexible insulative-conductive covering having approximately the same action as covering 20 in FIG. 1. The FIG. 3 covering has a surface area that is several times the surface area of the associated bandage 25, whereby heat is enabled to flow from healthy areas 15 of the person's skin through conductive layer 23 into bandage 25.

Figure 4:
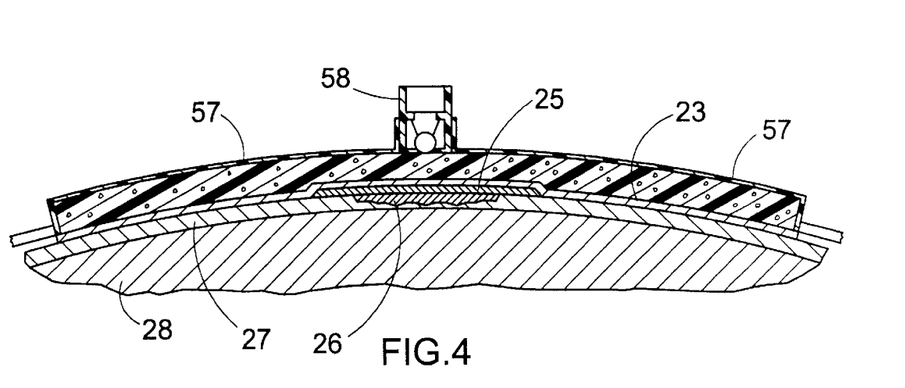
FIG. 4 is a fragmentary sectional view, taken in the same direction as FIG. 3, but showing a further embodiment of the invention.

FIG. 4 shows another form of the invention, wherein heat insulating layer 21 is formed of an elastomeric foam having open (communicating) cells. Various materials can be used as the cell wall material, including polyurethane, polyvinyl chloride, polyethylene, natural rubber, or snythetic rubber.

The heat-insulating foam is bonded to the heat-conducting layer 23, after which the exposed surfaces of the foam layer are sealed, as by a thin fluid-impervious film (envelope) 57. The communicating cells within foam sheet 21 are placed under a slight vacuum to enhance the insulating action of the foam layer. The communicating cells can be filled with any of the high insulative gases, such as air, argon, carbon dioxide, krypton, or freon to achieve maximum insulative properties.

As shown in FIG. 4, a check valve 58 is encapsulated by the plastic film 57 on foam sheet 21, to provide one way flow of gas from the foam cells to an evacuation pump (not shown). After the pump has been operated to establish the desired vacuum condition, the pump is disconnected from valve 58, leaving the valve in a closed condition for maintaining the foam cells at a sub-atmospheric pressure.

Figure 5:
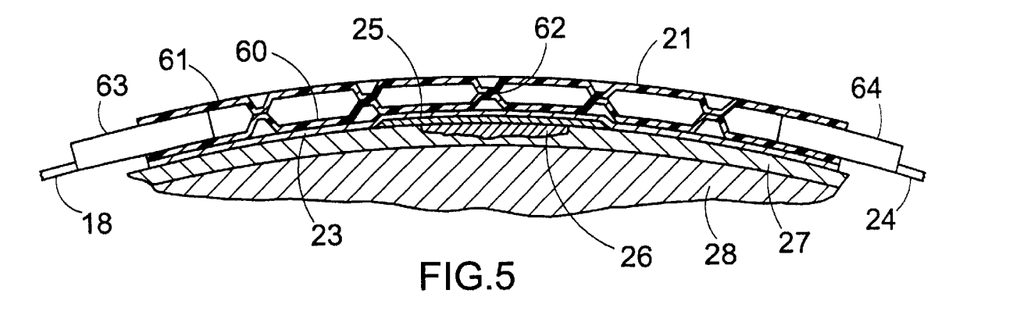
FIG. 5 is a fragmentary sectional view illustrating another form that the invention can take.

FIG. 5 shows a further embodiment of the invention, wherein the heat-insulating layer 21 comprises a hollow three-dimensional plastic sheet bonded to the upper surface of thermally-conductive layer 23. The sheet can be internally positioned and re-inforced so as to act as a gas containment device for a low conductive gas such as air, argon, carbon dioxide, krypton, nitrogen or freon.

In the FIG. 5 construction, heat-insulating layer 21 includes a thin plastic lower sheet 60, and a thin plastic upper sheet 61. Mating areas of the two sheets are embossed, as at 62, to form connection points for the sheets while achieving a desired sheet spacing. Edge areas of the sheets are heat sealed to isolate the cell(s) or chamber(s) from the ekternal atmosphere.

Figure 6:
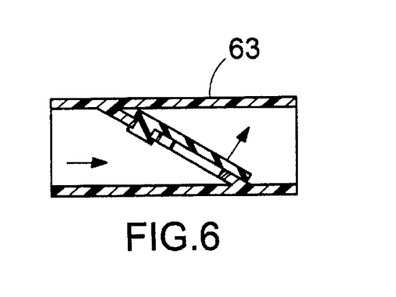
FIG. 6 shows a check valve used in the FIG. 5 embodiment.
Figure 7:
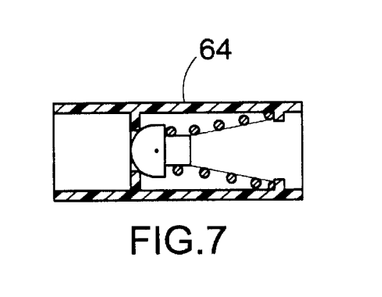
FIG. 7 shows a pressure relief valve employed in the FIG. 5 construction.

The cell(s) formed by sheets 60 and 61 are pressurized by means of a pump (not shown) that is connected to a gas check valve 63 suitably heat sealed to an edge area of the insulating layer. A pressure relief valve 64 is sealed to another edge area of the insulating layer to prevent over pressurization of the cell(s), and possible rupture of sheet 61.

When the pump is disconnected from check valve 63 the check valve prevents gas escape from the cell(s). Various gases can be used to pressurize the cells in the FIG. 5 construction, including air, nitrogen, argon, carbon dioxide, krypton, nitrogen or freon. An advantage of the FIG. 5 construction is the relatively low weight of the heat-insulating layer 21. Sheets 60 and 61 can be relatively thin (light) plastic sheets.

Cell pressurization, in combination with the limb encirclement pressure of straps 24 and 18, tends to pressurize the fit of thermally conductive layer 23 on the person's skin, so that thermal resistance at the interface between the person's skin and conductive layer 23 is somewhat minimized.

It will be appreciated that the heat-insulator sheet constructions depicted in FIGS. 1, 3, 4 and 5 are illustrative of various heat barrier arrangements that can be employed in practice of the invention. Other flexible heat insulator sheets can be used, e.g. a very high insulative sheet known as "aeroger". One commercially available flexible aerogel material is marketed under the trademark SPACELOFT by Aspen Aerogel, Inc. of Malborough, Mass. A principal feature of the invention is a two layer system that includes a thermally conductive inner layer for transmitting body heat from healthy areas of the person's skin to a bandage overlying a skin wound, and a heat-insulating outer layer overlying the thermally minimized heat loss from the thermally conductive layer and the tissue underneath.

FIGS. 8 through 13 show various ways or mechanisms that can be used to secure the insulative-conductive covering on a person's body, so that the conductive layer is in thermal contact with the person's skin.

Figure 8:
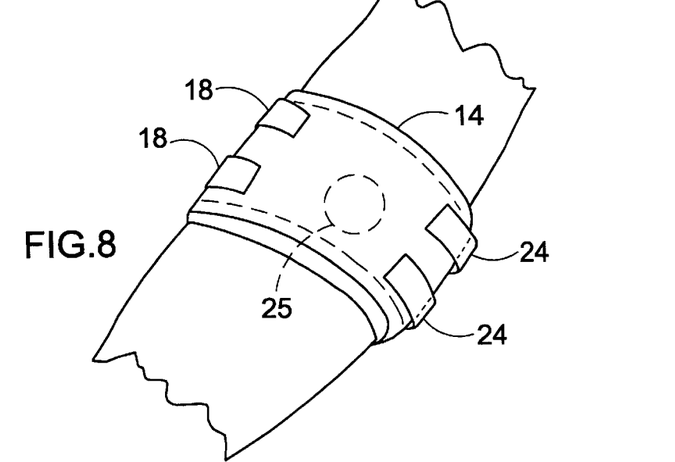
FIG. 8 is a perspective view showing the FIG. 1 wound treatment device in place on the arm or leg of a person.

FIG. 8 shows the insulative-conductive covering in surrounding relation to the shin or calf area of a person's leg. The covering is retained in place by means of flexible straps 18 and 24. The terminal ends of the straps (not shown) carry hook-and-loop patches that mate to maintain the covering in firm engagement with the person's skin (and the wound bandage).

Figure 9:
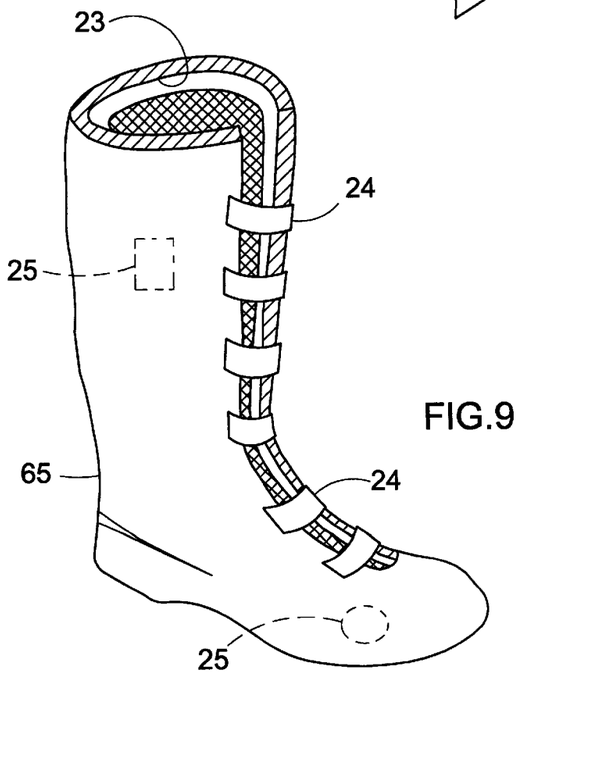
FIG. 9 is a perspective view of a boot that incorporates a wound treatment device of the present invention.

FIG. 9 shows the wound treatment device as being incorporated into a flexible boot 65 that is sized to fit a person's foot. The boot wall is formed of multi-layer insulative-conductive material, e.g. the material shown in FIG. 1. The inner layer of this material (facing the person's skin) is thermally conductive, whereby body heat is enabled to flow from healthy areas of the person's skin into the thermally conductive inner layer to maintain bandage 25 at a close to the normal core body temperature 37° C. The boot can be maintained in a closed condition by means of straps 24. Each strap may have a hook-and-loop patch that mates with an interlocking patch located on the registering outer surface of the boot.

Figure 10:
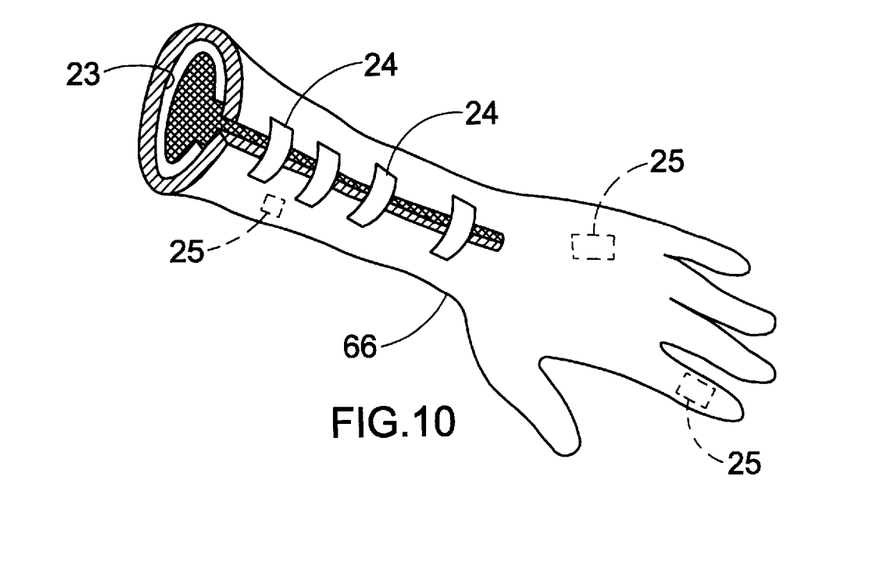
FIG. 10 is a perspective view, showing a wound treatment device of t he present invention incorporated into a glove.

FIG. 10 shows a flexible glove 66 having the insulative-conductive covering of the present invention incorporated therein, whereby the glove can be applied to a person's hand for covering one or more wound bandages on the person's hand or forearm.

Figure 11:
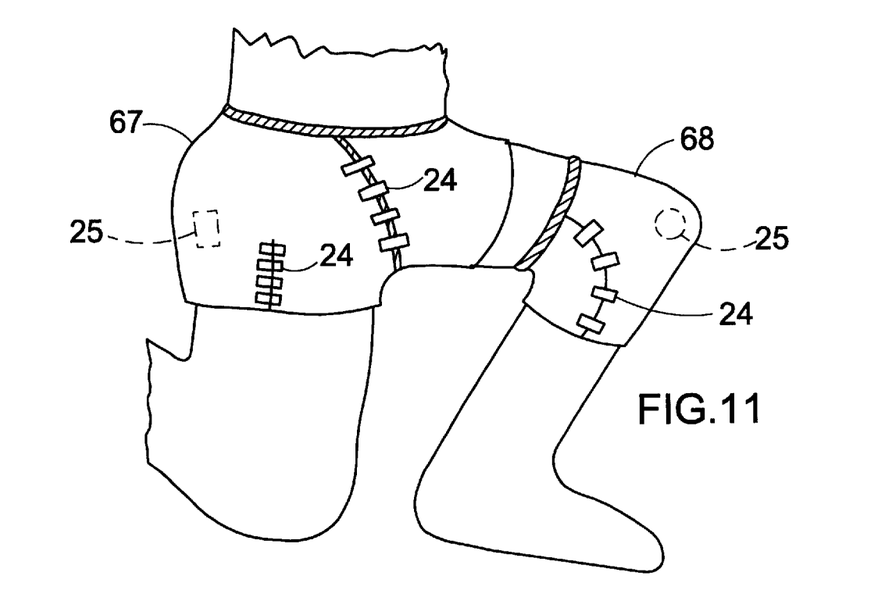
FIG. 11 shows an underpants and a knee covering in place on a person. A wound treatment device of the present invention is included in the wall structure of the underpants and knee covering.

FIG. 11 shows the invention incorporated into two articles of clothing, namely a pant 67 and a knee covering 68. These articles of clothing can be used to treat wounds on a person's buttocks, hips and knees.

Figure 12:
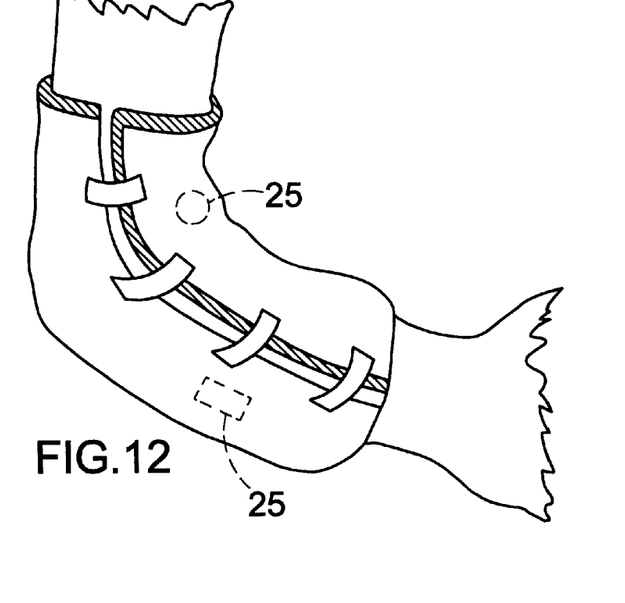
FIG. 12 shows an elbow covering having a wound treatment device of the present invention.
Figure 13:
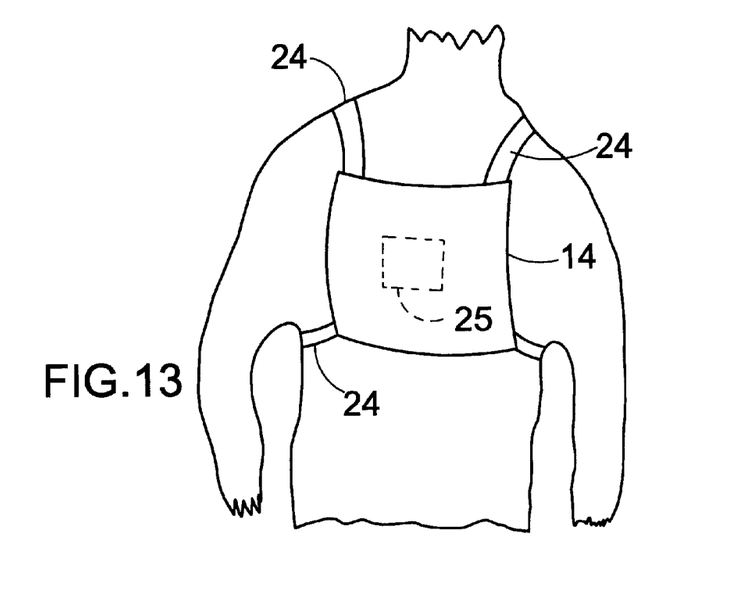
FIG. 13 shows the invention incorporated into a wound treatment device for a person's back or chest.

FIG. 12 shows the invention applied to (or incorporated in) a sleeve for a person's elbow. FIG. 13 shows a wound treatment device of the present invention constructed for use on a person's back or chest.

It will be appreciated that the drawings and descriptive are illustrative of the invention, and that the invention can be practiced in various forms and configurations.

What is claimed is:
1. A wound treatment device for a skin wound, comprising:
   a. a wound treatment bandage adapted to overlie a wound on a person's skin, the bandage having a peripheral edge spaced away from the skin wound so that the bandage completely covers the wound;
   b. a flexible insulative-conductive covering for said bandage, the flexible insulative-conductive covering having inner and outer layers, said inner layer being adapted to overlie the bandage and healthy areas of a person's skin surrounding the wound, said outer layer being adhered to said inner layer so as to completely conceal said inner layer when said covering is in place on the bandage;
   c. said inner layer being made of a thermally conductive material adapted to be in direct contact with the per- son's skin for conducting human body heat from the healthy areas of the skin along said inner layer into the bandage;

d. said outer layer being made of a heat insulating material for preventing body heat from escaping from said inner layer; and e. said outer layer having a surface area that is at least as large as the surface area of said inner layer;

f. whereby said outer layer completely covers said inner layer, and the inner layer surface of said flexible covering having a surface area that is several times the surface area of the wound treatment bandage such that heat flows from healthy areas of the person's skin along the thermally conductive inner layer, to maintain the bandage at a temperature that is approximately the same as that of the healthy skin surrounding the wound.

2. The wound treatment device in accordance with claim 1, wherein the surface area of the flexible covering is at least ten times the surface area of the bandage.

3. The wound treatment device in accordance with claim 1, ewherein said heat-insulting outer layer is formed of an elastomeric foam.

4. The wound treatment device in accordance with claim 3, wherein said elastomeric foam is filled with a low conductivity gas.

5. The wound treatment device in accordance with claim 3, wherein said elastomeric foam is a material selected from polyurethane, polyvinyl chloride, polyethylene, natural rubber, synthetic rubber, or silicone rubber.

6. The wound treatment device in accordance with claim 3, wherein said elastomeric foam is a closed cell foam material.

7. The wound treatment device in accordance with claim 6, wherein said closed cell foam material is filled with a low conductivity gas.

8. The wound treatment device in accordance with claim 1, wherein said heat-insulating outer layer is formed of an open-cell foam sheet, and a fluid-impervious film envelope sealing the entire external surface of said foam sheet.

9. The wound treatment device in accordance with claim 8, wherein the said open-cell foam sheet is filled with a low conductivity gas.

10. The wound treatment device in accordance with claim 1, wherein said heat-insulating outer layer is formed of a laminated plastic sheet having plural closed bubbles spaced along the sheet surface.

11. The wound treatment device in accordance with claim 10, wherein said closed bubbles are filled with a low conductivity gas.

12. The wound treatment device in accordance with claim 1, wherein said heat-insulating outer layer comprises a three dimensional sheet defining at least one closed cell spanning the sheet surface.

13. The wound treatment device in accordance with claim 12, wherein each said cell is pressurized with a low conductivity gas.

14. The wound treatment device in accordance with claim 13, wherein the low conductivity gas is selected from the group consisting of air, nitrogen, carbon dioxide, krypton, or freon.

15. The wound treatment device in accordance with claim 12, wherein each said cell is partially evacuated to have a sub-atmospheric internal pressure.

16. The wound treatment device in accordance with claim 1, wherein said inner layer consists of a thermally conductive foil adapted to have direct contact with the person's skin.

17. The wound treatment device in accordance with claim 16, wherein said thermally conductive foil is selected from the group consisting of silver, gold, copper, aluminum, aluminum alloy, and carbon composites.

18. The wound treatment device in accordance with claim 1, wherein said thermally conductive inner layer comprises a woven gauze formed of thermally-conductive screening material.

19. The wound treatment device in accordance with claim 1, wherein said bandage includes thermally conductive material for stabilizing the temperature of the skin wound.

20. The wound treatment device in accordance with claim 1, further comprising flexible strap means attached to said covering for attaching the wound treatment device to a person's body, said strap means comprising oppositely extending strap sections adapted to encircle a part of the person's body so that the thermally-conductive inner layer is maintained in surface contact with the bandage and healthy areas of the person's skin.

21. The wound treatment device in accordance with claim 1, wherein said flexible covering is configured as a flexible boot for application to a person's foot.

22. The wound treatment device in accordance with claim 1, wherein said flexible covering is configured as a flexible glove for application to a person's hand.

23. The wound treatment device in accordance with claim 1, wherein said flexible covering is configured as a flexible sheet having sufficient area to substantially encircle a person's arm or leg.

24. The wound treatment device in accordance with claim 1, wherein said flexible covering is configured as a pant to treat wounds on a person's buttocks and hips.

25. The wound treatment device in accordance with claim 1, wherein said flexible covering is configured as a knee covering to treat wounds on a person's knee.

26. The wound treatment device in accordance with claim 1, wherein said flexible covering is configured as an elbow covering to treat wounds on a person's elbow.

27. The wound treatment device in accordance with claim 1, wherein said flexible covering is configured as a flat patch to treat wounds on a person's back or chest.

28. The wound treatment device in accordance with claim 1, wherein said thermally-conductive inner layer comprises a woven gauze formed of thermally-conductive screening serial bonded onto thermally conductive foil.

29. The wound treatment device in accordance with claim 1 wherein the flexible covering consists of only a heat insulative outer layer without the thermally conductive inner layer.

30. The wound treatment device in accordance with claim 1 wherein the flexible covering consists of just a thermally conductive inner layer without the heat insulative outer layer.

31. The wound treatment device in accordance with claim 1 wherein said heat insulating outer layer is formed of an aerogel based on precursor materials consisting of silica, alumina, titania, hafnium carbide or carbon.

* * * * *